United States Patent [19]

Brody

[11] Patent Number: 5,288,290
[45] Date of Patent: Feb. 22, 1994

[54] MULTI-PORTED VALVE ASSEMBLY

[75] Inventor: George Brody, San Clemente, Calif.

[73] Assignee: Alcon Surgical, Inc., Fort Worth, Tex.

[21] Appl. No.: 23,165

[22] Filed: Feb. 19, 1993

Related U.S. Application Data

[63] Continuation of Ser. No. 765,617, Sep. 25, 1991, abandoned.

[51] Int. Cl.$^5$ .............................................. A61M 5/178
[52] U.S. Cl. .......................................... 604/32; 604/35; 604/248; 604/258; 604/902; 137/625.47; 251/904
[58] Field of Search .................... 604/30, 32, 35, 118, 604/82, 248, 290, 902, 93, 258; 137/876, 887, 625.41, 625.46, 625.47; 251/310, 904

[56] References Cited

U.S. PATENT DOCUMENTS

| | | |
|---|---|---|
| D. 271,421 | 11/1983 | Fetterman . |
| 706,928 | 8/1902 | Graham . |
| 732,010 | 6/1903 | Savage . |
| 1,236,865 | 8/1917 | Pittenger ........................ 604/258 |
| 1,710,540 | 4/1929 | Hollander ........................ 604/32 |
| 1,853,202 | 4/1932 | Catlin ........................ 604/32 |
| 2,821,998 | 2/1958 | Mayhew . |
| 2,854,027 | 9/1958 | Kaiser et al. ........................ 604/248 |
| 3,057,350 | 10/1962 | Cowley ........................ 137/625.41 |
| 3,276,472 | 10/1966 | Jinkens et al. ........................ 604/248 |
| 3,481,367 | 12/1969 | Deuschle ........................ 137/625.47 |
| 3,618,637 | 11/1971 | Santomieri . |
| 3,771,765 | 11/1973 | Scapes ........................ 137/625.47 |
| 3,774,604 | 11/1973 | Danielsson ........................ 137/625.47 |
| 3,780,736 | 12/1973 | Chen ........................ 604/32 |
| 3,783,900 | 1/1974 | Waldbillig ........................ 137/625.47 |
| 3,791,379 | 2/1974 | Storz ........................ 137/625.47 |
| 3,834,372 | 9/1974 | Turney . |
| 4,146,055 | 3/1979 | Ryder et al. ........................ 137/625.41 |
| 4,219,021 | 8/1980 | Fink ........................ 604/248 |
| 4,314,586 | 2/1982 | Folkman . |
| 4,410,001 | 10/1983 | Goguen . |
| 4,522,233 | 6/1985 | Mojadad ........................ 137/625.47 |
| 4,604,093 | 8/1986 | Brown et al. . |
| 4,662,871 | 5/1987 | Rafelson ........................ 604/250 |
| 4,721,133 | 1/1988 | Sundblom . |
| 4,758,235 | 1/1988 | Tu . |
| 4,790,193 | 12/1988 | Moriuchi et al. ........................ 137/625.47 |
| 4,820,280 | 4/1989 | Berch et al. ........................ 604/248 |
| 4,904,245 | 2/1990 | Chen et al. ........................ 604/248 |
| 4,950,230 | 8/1990 | Kendell ........................ 604/32 |
| 5,074,334 | 12/1991 | Onodera . |

Primary Examiner—C. Fred Rosenbaum
Assistant Examiner—Mark Bockelman
Attorney, Agent, or Firm—James Arno; Julie Cheng; Christopher W. Brody

[57] ABSTRACT

The multi-ported valve assembly includes a valve body having a plurality of individual ports disposed in a common plane and a common port having its axis disposed perpendicularly to the common plane of the individual ports. The valve assembly includes a selector means having a body portion designed to engage the valve body and provide selective communication between one of the individual ports and the common port. The selector means includes a handle to facilitate rotation thereof and selection of a desired fluid flow passageway as well as indicator means to indicate direction of fluid flow. Also provided are sealing means to prevent external leakage during use and suitable connecting or coupling means to provide connection especially in devices and apparatus used in ophthalmic surgical procedures.

12 Claims, 3 Drawing Sheets

MULTI-PORTED VALVE ASSEMBLY

This application is a continuation of application Ser. No. 07/765,617 filed Sep. 25, 1991 now abandoned.

FIELD OF THE INVENTION

The present invention is directed to multi-ported valve assembly particularly for use in surgical or medical applications. The valve assembly includes a valve body having a plurality of first ports disposed in a common plane. The valve body also includes a second port whose axis is configured perpendicular to the common plane. The valve assembly also provides a selector means which establishes communication between one of the first ports and the second port as well as indicating direction of fluid flow through the valve. The selector means engages the valve body generally opposite the second port to prevent entanglement of tubing or conduit during rotation thereof.

BACKGROUND ART

In the prior art, numerous multi-ported valves have been proposed to control a plurality of fluid flow streams. U.S. Pat. Nos. 706,928 to Graham and 2,821,998 to Mayhew disclose these types of valves. Each of the patents to Mayhew and Graham disclose a manifold-type valve which provides communication between one inlet and a plurality of outlets. The teachings of these two patents are different from that of the present invention in that neither Mayhew or Graham disclose a valve device which provides connection between a single common port and one of a plurality of additional ports aligned in a different, but common plane.

U.S. Pat. No. 4,410,001 to Goguen discloses an antisiphon selector valve having both input and output ports lying in the same plane. U.S. Pat. No. 732,010 to Savage discloses another fluid controlling valve which includes a chamber and a disk valve to control fluid flow from an inlet port to one or both outlet ports. The teachings of Goguen and Savage are different from the present invention in that neither patent teaches or fairly suggest all of the features of the present invention including a valve body in combination with a selector means, the selector means providing connection between an inlet and outlet port via a passageway similar in diameter to the inlet and outlet ports.

Multi-ported valves have also been proposed for use in medical or surgical applications. U.S. Pat. Nos. 3,618,637 to Santomieri, 4,604,093 to Brown et al., 4,721,133 to Sundblom, 4,758,235 to Tu and Design Patent Number 271,421 to Fetterman disclose these types of valves. The design patent to Fetterman discloses a medical valve wherein the common port is integral with the selector handle. In contrast, the multiported valve of the present invention provides a selector handle which is remote from the common port. The patent to Santomieri discloses a valve having a mixing chamber therein to accommodate simultaneous infusion and mixing of a plurality of fluids into a single infusion tube. No such mixing chamber is contemplated by the present invention.

The valve disclosed by U.S. Pat. No. 4,758,235 to Tu is designed to provide connection between one of a multiplicity of syringes to a patient. The valve of Tu is different from the proposed multiported valve assembly in that Tu includes female luer fittings to engage syringes, provides different sealing means between the valve body and selector and has the outlet port disposed in a plane parallel to the plane containing the plurality of inlet ports. U.S. Pat. No. 4,721,133 to Sundblom discloses a valve for use in the field of opthalmic surgery which includes a deformable but resilient sealing member which is deformed to prevent fluid transmission through a channel in the valve. U.S. Pat. No. 4,604,093 to Brown et al. discloses a valve similar to that disclosed by Tu which also includes gear means, control means and drive means to provide automatic administering of fluids.

In view of the prior art, a need has developed to provide a less complicated multi-ported valve assembly which is adaptable to different types of medical procedures which may include a single inlet with a plurality of outlets or a single outlet with a plurality of inlets. For example, in ophthalmic surgery, a source of vacuum may be desired to be connected to a plurality of different instruments requiring vacuum or, in the alternative, a plurality of irrigation fluid sources may be required to be connected to a single infusion outlet.

In response to this need, the present invention provides an improved multi-ported valve assembly has been developed which provides a means to connect a single common port with one of a plurality of individual ports or to a shut-off position. The multiported valve assembly includes a selector handle which includes an indicator to indicate direction of flow through the valve. The individual ports are disposed in a plane perpendicular to the outlet or common port to prevent entanglement of tubing connected to the various ports. In addition, the selector is configured opposite the common port to further facilitate ease of selection of a particular flow direction.

SUMMARY OF THE INVENTION

It is an object of the present invention to provide an improved multi-ported valve assembly, especially for use in medical procedures such as ophthalmic surgery.

It is a further object of the present invention to provide a unitary valve assembly which connects a common port to one of a plurality of individual ports for providing fluid flow to or from the common port, or to shut off the flow.

It is a still further object of the present invention to provide a multi-ported valve assembly for use in ophthalmic surgery wherein a source of vacuum may be connected to one of the plurality of surgical instruments. Alternatively, a source of irrigation fluid may be directed to one of a plurality of irrigating surgical instruments.

It is yet a further object of the present invention to provide a multi-ported valve assembly which includes a selector handle configured remotely from individual or common ports to minimize entanglement of tubing or conduit during use.

In satisfaction of the foregoing objects and advantages, there is provided a multi-ported valve assembly which includes a valve body having a plurality of individual ports and a single common port extending outwardly therefrom. The individual ports are aligned in the common plane which is generally perpendicular to the axis of the common port. The valve assembly also includes a selector means which is designed to engage the valve body and provide communication between one of the individual ports and the common port. The selector means includes a handle thereon to facilitate rotation thereof and indicia means to indicate direction of flow. The valve assembly may be used in surgical applications such as ophthalmic surgery to connect a single vacuum source to a plurality of surgical instruments.

In a further embodiment, the indicia means may be adjustable so as to indicate direction of flow through the valve. The valve assembly also includes sealing means to prevent external leakage of fluid flowing through the valve. The valve assembly may also be provided with coupling or connecting means to facilitate attachment to medical instruments or devices, such as cannulas or emulsifiers.

BRIEF DESCRIPTION OF DRAWINGS

Reference is now made to the Drawings accompanying the application wherein.

DESCRIPTION OF THE PREFERRED EMBODIMENTS

The present invention is concerned with a multiported valve assembly, particularly for use in surgical procedures in the field of ophthalmic surgery. The multi-ported valve of the present assembly offers advantages over prior art devices including easier operation and a compact and efficient design which results in lower manufacturing cost. In many prior art devices, the selector handle is disposed on the valve device in a location which causes entanglement with tubing or conduit connected to the valve. In contrast, the multi-ported valve of the present invention has the ports disposed such that the selector handle may be operated without interference with any connected tubing or conduit.

The multi-ported valve assembly permits flow of a fluid such as a gas or liquid from a common port to one of a plurality of individual ports. In addition, the multi-ported valve assembly permits flow in the opposite direction when selecting one of a plurality of source fluids to be directed to the common port. In the field of ophthalmic surgery, the multi-ported valve assembly may be utilized to provide a source of vacuum from a common source to one of a plurality of surgical instruments. Alternatively, a plurality of irrigation fluid sources may be selectively directed to a single surgical instrument such as an irrigation cannula. Last, the multi-ported valve may be used to shut off the fluid flow.

Figure 1:
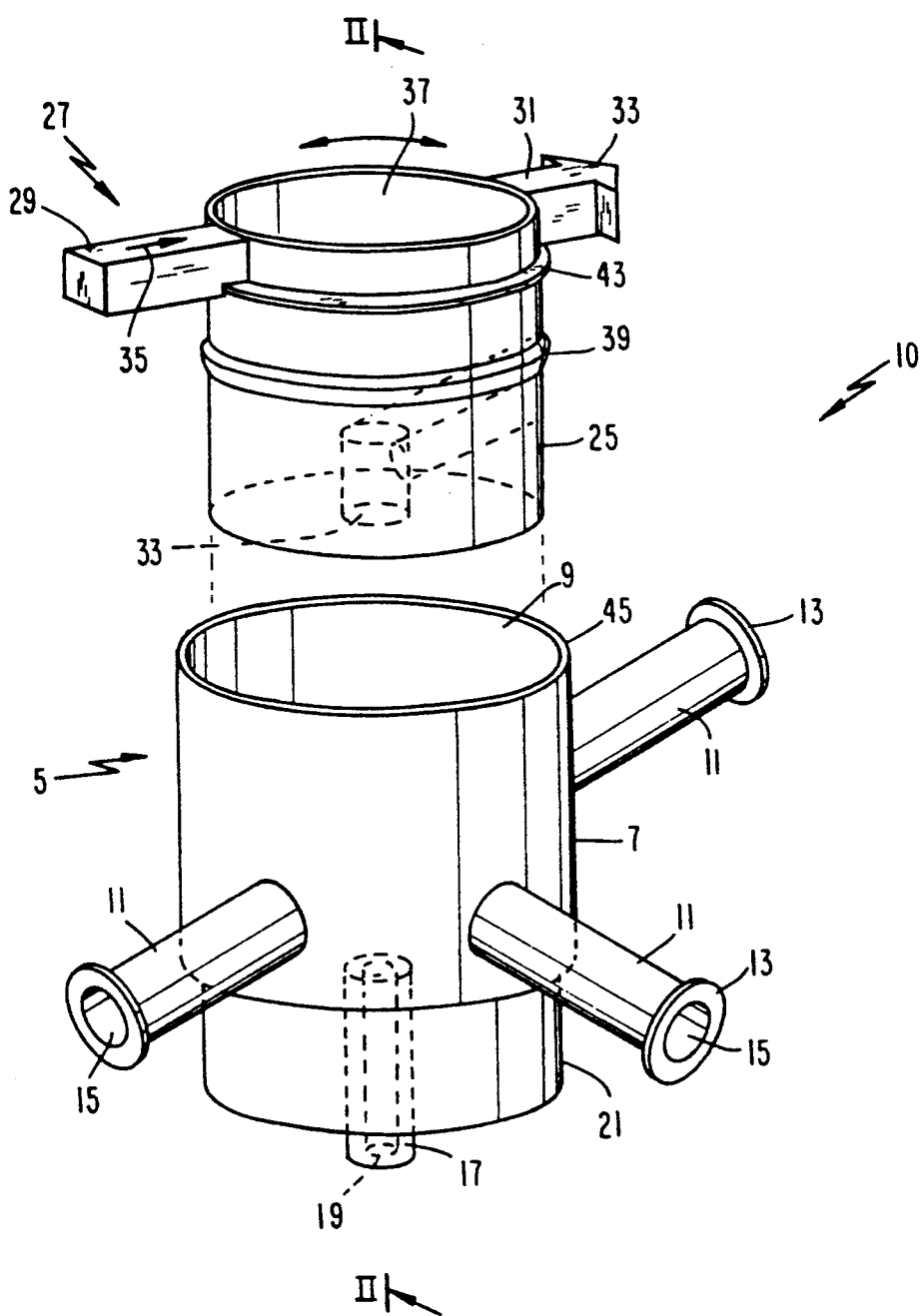
FIG. 1 shows a first embodiment of the valve assembly exploded to show greater detail.

In certain prior art devices, a mixing or intermediate chamber is provided between the inlet and the outlet flows. The valve of the present invention eliminates this internal chamber in the valve body and, consequently, eliminates the associated pressure drop therewith. As a result, the valve assembly provides improved performance in surgical procedures requiring precise control of operating conditions such as vacuum levels or the like. With reference now to FIG. 1, a first embodiment of the multi-ported valve assembly of the present invention is generally designated by the reference numeral 10 and is seen to include a selector means 3 and a valve body 5. The valve body 5 includes a cylindrical valve housing 7 having a chamber 9 therein. Extending outwardly from the valve housing 7 are a plurality of elongate tubular members 11, the elongate tubular members forming a plurality of individual ports 15 which provide access to the chamber 9. All of the elongate members 11 are disposed in a common plane. Each elongate tubular member 11 preferably include a flange portion 13 at the distal end thereof.

Extending downwardly from the valve housing 7 is an additional elongate member 17 which includes a port or passageway 19 therethrough which is in communication with the chamber 9.

The elongated tubular member 17 is surrounded by a cylindrical housing 21 having internal threads 23 thereon. The internally threaded housing 21 is designed to facilitate coupling or connecting the elongated tubular member 17 to a source of a fluid, a surgical instrument, a source of vacuum or the like. The flanges 13 on each of the elongated tubular members 11 also facilitate connection to these types of devices. Utilizing the flanges 13 and internally threaded connection 21 facilitate use of the multiported valve with instrumentation and devices typically used in ophthalmic surgery.

Still with reference to FIG. 1, the selector means 3 includes a selector means body portion 25 and a handle 27 thereon. The handle 27 comprises a first portion 29 extending outwardly from the selector means body portion 25 with a second portion 31 axially aligned with the first portion 29 and extending outwardly and diametrically opposite from the first portion 29. The second portion 31 may have on the distal end thereof an arrow shaped portion 33 to facilitate indicating direction of flow during use of the multi-ported valve assembly. In addition, the first portion 29 of the handle 27 may also include indicia means 35 in the shape of an arrow to further indicate direction of fluid flow.

Figure 2:
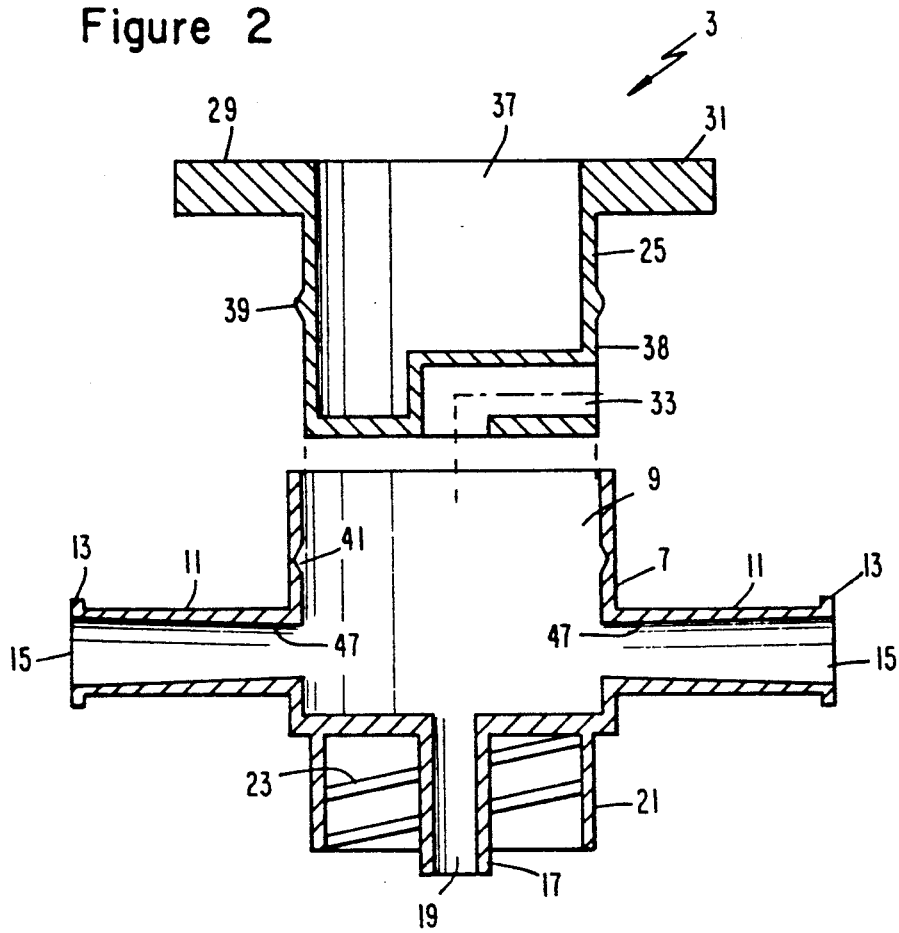
FIG. 2 shows a cross-sectional view along the line II—II depicted in FIG. 1.

With reference to FIGS. 1 and 2 now, the selector means body portion 25 may also include a chamber 37 therein and a solid portion 38 having a passageway 33 therethrough. The chamber 37 reduces the amount of material necessary for manufacture of the body portion 25, thereby reducing manufacturing cost and facilitating manufacture.

As can be seen in from FIG. 2, the selector means 3 is designed to be inserted into the chamber 9 of the valve housing 7. In this manner, the passageway 33 can provide communication between one of the ports 15 and the common port 19. The relationship between the individual ports 15 and the common port 19 is more clearly depicted in FIG. 2, wherein the ports 15 are in a common plane with the port 19 disposed perpendicularly to the common plane containing the ports 15.

The selector means 3 also includes a protrusion 39 surrounding the outer surface of the selector body portion 25. The protrusion 39 is designed to engage a channel 41 disposed circumferentially on the inner surface of the valve housing 7. Engagement of the protrusion 39 with the channel 41 provides a seal so as to prevent external leakage of fluid flowing through the valve assembly. It should be understood that the selector means 3 is designed with the valve body 5 to have sufficient flexibility to permit insertion of the selector means body portion 25 having the protrusion 39 thereon into the valve housing 7. Manufacturing the valve assembly components out of a plastic or non-metal material would permit suitable engagement of the components together while providing the proper sealing function.

Of course, other internal sealing means may be provided such as an 0-ring in substitution of the protrusion 39 on the selector means body portion 25.

The individual ports 15 may also include a taper as shown by the reference numeral 47 in FIG. 2.

With reference back to FIG. 1, the selector means 3 includes a flange 43 surrounding the selector means body portion 25. The flange 43 is designed to engage the top surface 45 of the valve housing 7 to provide proper alignment between the passageway 33 and the ports 15 and 19.

Figure 3:
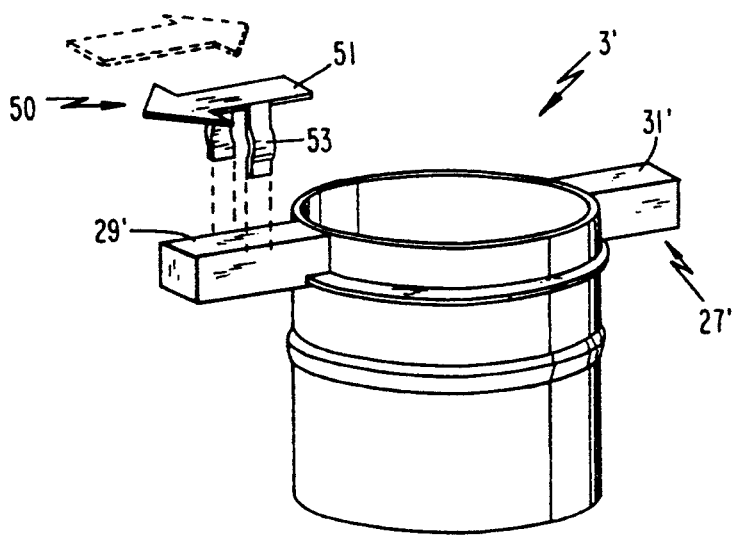
FIG. 3 shows a second embodiment of the selector means of the valve assembly of the present invention.

With reference to FIG. 3, a further embodiment of the selector means of the multi-ported valve assembly is generally designated by the reference numeral 3'. In this embodiment, the handle 27' includes indicia means 50 to accommodate indication of flow entering or exiting one of the individual ports 15. The handle 27' includes a first portion 29' and a second portion 31' which are axially aligned in a similar manner as the portions 29 and 31 depicted in FIG. 1. However, in substitution of the fixed indicia depicted in FIG. 1, and arrow 51 is provided having clip means 53 thereon to attach to the handle portion 29'. By providing a removable indicia means 50, and as shown in cross-hatch in FIG. 3, the arrow 51 may be removed and reversed to indicate flow in an opposite direction. It should be understood that other adjustable indicia means may be employed in combination with the selector means 3'. For example, the arrow 51 may include a pin extending therefrom which is designed to engage an opening either handle portion 29' or 31'. In this embodiment, the arrow 51 may merely be rotated between flow direction to indicate flow without removal and reattachment thereof.

Figure 4A:
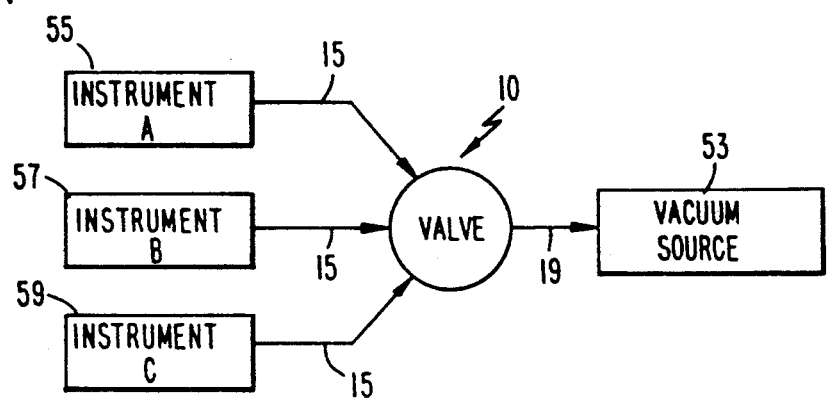
FIGS. 4A-4C depict schematic representations of different utilizations of the inventive valve assembly.
Figure 4B:
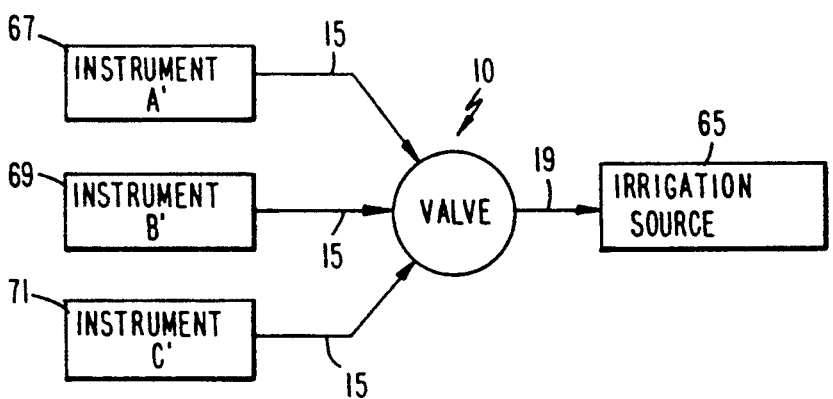
Figure 4C:
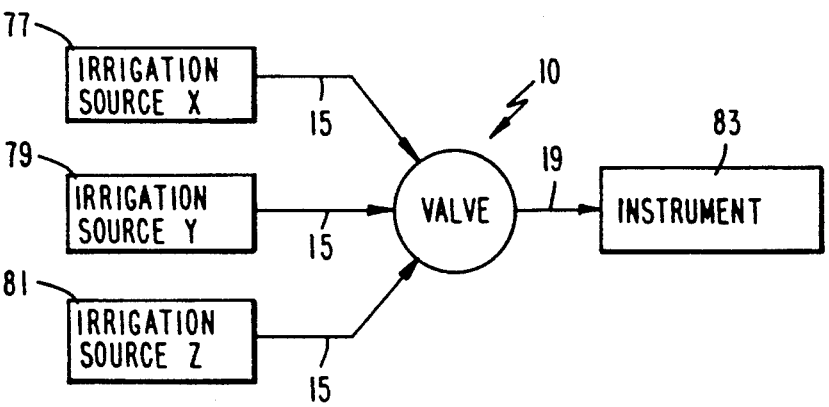

FIGS. 4A-4C depict exemplary uses of the multiported valve assembly 10 of the present invention. In FIG. 4A, the common port 19 of the valve assembly 10 is connected to a source of vacuum 53. Each of the individual ports 15 are connected to respective instruments 55, 57 and 59. In this manner, a source of vacuum may be provided to one of the instruments 55, 57 or 59 by rotation of the selector means 3 of the valve assembly 10. The arrows depicted in FIG. 4A indicate the direction of flow of fluid being aspirated, such direction being indicated by the indicating means 33, and 35 shown in FIG. 1 or indicator means 50 shown in FIG. 3.

Alternatively, and with reference to FIG. 4B, a single irrigation fluid source 65 may be connected to the valve assembly 10 via the common port 19. Connected to the individual ports 15 are plurality of instruments requiring irrigation fluid shown by the reference numerals 67, 69 and 71. In this configuration, a source of irrigation fluid may be selectively directed by operation of the valve assembly 10 to one of the instruments 67, 69 or 71. Using the valve assembly in this manner, the indicia means 50 may be utilized to indicate direction of flow towards one of the individual ports 15.

With reference to FIG. 4C, a plurality of irrigation fluid sources are provided, 77, 79 and 81, which are connected to individual ports 15, respectively. A single instrument 83 requiring irrigation fluid such as an irrigation cannula is connected to the common port 19. By rotation of the selector means 3 in the valve assembly 10, a particular source of irrigation fluid may be supplied to the instrument 83. In this manner, different types of irrigating fluids may be selectively applied to the instrument 83 depending on requirements of the particular surgical procedure.

Although the multi-ported valve assembly has been shown for use particularly in the field of surgical procedures, the multi-ported valve assembly is applicable to any use requiring selection of a particular direction of fluid flow and indication of the flow. In addition, although three individual ports have been illustrated, more ports may be provided extending outwardly from the valve housing 7 of the valve body 5.

As such, an invention has been disclosed in terms of preferred embodiment thereof which fulfill each and every one of the objects of the present invention as set forth hereinabove and provides a new and improved multi-ported valve assembly for use in selection of fluid flow direction.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:

1. A multi-ported valve assembly comprising:
   a) a hollow cylindrical first valve body having a generally cylindrical chamber therein, said chamber forming a first opening in said valve body, said valve body further comprising;
      i) a plurality of first ports extending outwardly from said valve body, and being disposed in a common plane; and
      ii) a second port extending outwardly from said valve body, the axis of said second port being substantially perpendicular to said common plane;
   b) a selector comprising a generally cylindrical body having an axis aligned with said second port axis, said generally cylindrical body having a first portion positioned in said generally cylindrical chamber and a second portion disposed outside of said cylindrical chamber, said second portion including a handle extending outwardly for rotating said cylindrical body, a passageway internal to said first portion for providing communication between said second port and one of said first ports or a shut-off position when said handle is rotated about said axis of said generally cylindrical body to a predetermined position, said generally cylindrical body including a second opening in said second portion and part of said first portion;
   c) a recess on an inner wall of said chamber of said valve body and a protrusion on an outer wall of said first portion of said cylindrical body, said protrusion engaging said recess to prevent external leakage of fluid flowing through said valve and to maintain relative positions of said valve body and said selector, said recess positioned between said common plane and said first opening of said valve body; and
   d) indicator means for indicating direction of a fluid flowing through said valve.

2. The valve assembly of claim 1 wherein said indicator means further comprises adjustable indicia means to permit indication of direction of fluid flow in one of said first ports.

3. The valve assembly of claim 1 wherein said handle further includes an arrow-shaped portion for indicating direction of fluid flow in one of said first ports.

4. The valve assembly of claim 2 wherein said adjustable indicia means includes an arrow-shaped clip removably attached to a portion of said handle to indicate direction of fluid flow in one of said first ports.

5. The valve assembly of claim 1 wherein each of said first ports further comprises a hollow elongated member having a tapered inner diameter and a coupling means on the distal end thereof.

6. The valve assembly of claim 1 wherein said second port comprises a hollow elongated member and means to couple said member to an ophthalmic surgical device.

7. The valve assembly of claim 6 wherein said means to couple said member further comprises a generally cylindrical housing surrounding at least a portion of said hollow elongate member and having threads therein for facilitating coupling to an ophthalmic surgical device.

8. The valve assembly of claim 1 further comprising a generally cylindrical housing surrounding at least a portion of said second port and having internal threads thereon for facilitating coupling said second port to an ophthalmic surgical device.

9. The valve assembly of claim 1 wherein said second port is removably connected to a source of vacuum and each of said first ports are removably connected to a surgical instrument requiring a source of vacuum for operation.

10. The valve assembly of claim 1 wherein said second port is removably connected to a source of irrigation fluid and each of said first ports is removably connected to a surgical instrument requiring a source of irrigation fluid for operation.

11. The valve assembly of claim 1, wherein each of said first ports is removably connected to a source of irrigation fluid and said second port is removably connected to a surgical instrument requiring a source of irrigation fluid for operation.

12. The valve assembly of claim 1 wherein said valve assembly is made entirely of a plastic material.

* * * * *